United States Patent [19]

Blank et al.

[11] Patent Number: 4,760,094

[45] Date of Patent: Jul. 26, 1988

[54] SPRAY DRIED ACETAMINOPHEN

[75] Inventors: Robert G. Blank, Vineland; Dhiraj S. Mody, Hammonton; Gary R. Agism, Cherry Hill; Richard J. Kenny, Sommerset, all of N.J.

[73] Assignee: American Home Products Corporation (Del.), New York, N.Y.

[21] Appl. No.: 921,658

[22] Filed: Oct. 21, 1986

[51] Int. Cl.$^4$ .............................................. A61K 31/74
[52] U.S. Cl. ..................................... 514/629; 424/78; 424/464; 424/499
[58] Field of Search ................ 514/629; 424/464, 499, 424/78

[56] References Cited

U.S. PATENT DOCUMENTS 4,439,453  3/1984  Vogel .................................. 514/629
4,631,284  12/1986  Salpepar et al. ................... 514/629

FOREIGN PATENT DOCUMENTS 58-172311  10/1983  Japan .

Primary Examiner—Joseph L. Schofer
Assistant Examiner—Peter F. Kulkosky
Attorney, Agent, or Firm—John W. Routh

[57] ABSTRACT

A therapeutic taste-neutral powder form of acetaminophen obtained by spray-drying a dispersion of acetaminophen and ethyl cellulose in water having a plasticizer dissolved or suspended therein.

4 Claims, No Drawings

SPRAY DRIED ACETAMINOPHEN

BACKGROUND OF THE INVENTION (a) Field of the Invention

This invention relates to a novel therapeutic form of spray dried acetaminophen having a neutral taste which can be formulated into, for example, chewable tablets and fast dissolving dosage forms as described in U.S. Pat. Nos. 4,305,502 and 4,371,516. More specifically this invention relates to a taste neutral spray dried powder formed by spray drying a dispersion of acetaminophen and ethylcellulose in water having a plasticiser dissolved or suspended therein. By taste-neutral it is meant that the powder has essentially no taste and is not sweet nor bitter.

(b) Prior Art

Acetaminophen, a widely used analgesic and antipyretic, is not palatable enough to be used in chew-type tablets for those people who do not swallow whole solid-type dosage forms.

The use of flavor agents e.g. chocolate, banana, orange, lemon, licorice, root beer, and raspberry, in particular, have been proposed for bitter tasting drugs. These agents are not dependable masking ingredients. Mint flavors can be useful in ameliorating a chalky taste parameter. Bitter properties, however, are very difficult to mask to any great extent, particularly, when they do not mimic the expected natural taste of the flavor agent.

Other properties including mouthfeel also need to be addressed in consideration of the oral acceptance of chewable or chew-type tablets.

The fast dissolving dosage forms described in U.S. Pat. Nos. 4,305,502 and 4,371,516 are manufactured to disintegrate in water within five seconds or less and hence dissolve rapidly in the saliva of the mouth. Heretofore the use of such dosage forms was restricted to pharmaceuticals which had a neutral taste or a slightly disagreeable taste which could be masked by a flavoring agent. Pharmaceuticals with a bitter taste such as acetaminophen and ibuprofen, however, could not heretofore be used in such dosage forms.

SUMMARY OF THE INVENTION

According to this invention, a novel therapeutic taste-neutral powder form of spray-dried acetaminophen is provided which can be formulated into chewable tablets and the like. The powder is formed by spray drying a dispersion of acetaminophen and ethyl cellulose in water having a plasticiser dissolved or suspended therein.

According to another aspect of this invention, a pharmaceutical dosage form for oral administration as a solid is provided, which dosage form can be disintegrated by water at 37° C. within ten seconds, and comprises as the pharmaceutical agent incorporated therein the taste neutral powder form of spray dried acetaminophen of this invention.

DETAILS OF THE INVENTION

The acetaminophen useful in this invention is the pharmaceutical grade. The ethyl cellulose useful in this invention is also National Formulary or pharmaceutical grade. Suitable grades are the AQUACOAT brand marketed by FMC Corporation of Newark, N.J. and the SURELEASE brand marketed by Colorcon Incorporated, West Point, Pa.

The plasticisers useful in this invention include dibutyl sebacate, glycerin, propylene glycol, triacetin and low molecular weight polyethylene glycols such as CARBOWAX 600, marketed by Union Carbide Corp. of Danbury, Conn. A suitable plasticizer is UNIFLEX brand of dibutyl sebacate marketed by Union Camp Corp. of Jacksonville, Fla.

The weight percent of acetaminophen in the taste neutral powder can be from about 63% to 77% by weight and the weight percent of the ethylcellulose can range from 15% to 30% by weight. At 15% by weight of ethylcellulose, there is no bitter taste and the powder is taste neutral. The weight percent of plasticizer in the taste neutral powder can be from about 2% to 7% by weight.

Spray dryers can be of the usual laboratory or commercial type. Suitable spray dryers are manufactured by Buchi Laboratoriums-Technik AG, by the Anhydro Company of Attleboro, Mass. and by Niro Atomizer Inc., of Columbia, Md.

The following examples illustrate the formation of the taste-neutral spray dried acetaminophen powder of the invention. In these examples, the ethyl cellulose was obtained from FMC Corporation, Newark, N.J. as AQUACOAT. It was a 30% solids dispersion in water of the standard type having a viscosity designation of 10 and an ethoxy content of 48.0% to 49.5%.

EXAMPLE I

In this example, the feed mixture to the spray dryer was composed of the following materials.

| Ingredient | Weight % Solids in powder | Grams Ingredient in suspension |
|---|---|---|
| Acetaminophen, USP | 70 | 210 |
| AQUACOAT brand of Ethyl Cellulose, NF | 25 | 249 |
| Uniflex brand of Dibutyl Sebacate | 5 | 15 |
| Deionized Water- | — | 1200 |
| Total: | 100% | ≈1674 grams |

Approximately 280 grams of finely divided acetaminophen was passed through a 35 mesh (Tyler) screen and 210 grams of the screened acetaminophen was dispersed in 1200 grams of deionized water using a homogenizer mixer. The dispersion was then mixed with a Lightnin mixer while adding 249 grams of AQUACOAT brand of ethyl cellulose as a 30% solids dispersion in water followed by the 15 grams of dibutyl sebacate. The mixing was continued for 75 minutes. The dispersion was then transferred to the feed hopper of the Buchi Portable Spray Dryer.

The spray dryer employed in this example was a Buchi 190 Mini Spray Dryer. The operating conditions for the Buchi Mini Spray Drier are customarily an inlet temperature of 220° C. and an outlet temperature of 130° C.

The spray drier was operated such that an air inlet temperature of approximately 210° C. and an air outlet temperature of approximately 140° C. was maintained throughout the run.

The product was a white, fine powder. The product upon tasting produced no bitterness characteristic of acetaminophen and was practically tasteless.

Dissolution data were obtained on capsules containing the spray dried product of this example using the USP procedure. The spray dried product in the amount of 114 milligrams containing 80 milligrams of acetaminophen was placed in each capsule and six capsules were used in each test. The data show that at a pH of 5–7 seventy-five percent of the acetaminophen was dissolved from one-half of the capsules in about 20 to 30 minutes and dissolution of seventy-five percent of the acetaminophen was not achieved in 30 minutes in the other one-half of the capsules.

EXAMPLE 2

In this example, the feed mixture to the spray dryer was composed of the following materials.

| Ingredient | Weight % Solids in powder | Grams Ingredient in suspension |
|---|---|---|
| Acetaminophen, USP | 70 | 140 |
| AQUACOAT brand of Ethyl Cellulose, NF | 25 | 166 |
| Uniflex brand of Dibutyl Sebacate | 5 | 10 |
| Deionized Water | — | 1600 |
| Total: | 100% | ≈1916 grams |

Approximately 160 grams of finely divided acetaminophen were passed through a 20 mesh (Tyler) screen and 140 grams of the screened acetaminophen were dispersed in 1600 grams of deionized water contained in a mixing vessel equipped with a Lightnin mixer. The dispersion was then mixed for 10 minutes. 166 grams of AQUACOAT brand of ethyl cellulose as a 30% solids dispersion in water were then added and mixed for 10 minutes and then the 10 grams of dibutyl sebacate were added. The dispersion was then transferred to the feed hopper of the spray dryer.

The spray dryer employed in the following example was a Niro Portable Spray Dryer, Model No. 21231-0001. The operating conditions include a variable air inlet temperature, a variable outlet temperature, a variable air pressure of compressed air driving the atomizer wheel, and a variable feed rate.

The spray drier was operated such that an air inlet temperature of approximately 150° to 155° C. was maintained throughout the run. An air outlet temperature was recorded at 100°–105° C.

The product was a fine, white powder which had a neutral taste.

EXAMPLE 3

In this example, the feed mixture to the spray dryer was composed of the following materials.

| Ingredient | Weight % Solids in powder | Grams Ingredient per 2 kg suspension |
|---|---|---|
| Acetaminophen, USP | 71.8 | 125 |
| AQUACOAT brand of Ethyl Cellulose, NF | 25.7 | 148.6 |
| Uniflex brand of Dibutyl Sebacate | 2.5 | 4.4 |
| Deionized Water | — | 1722 |
| Total: | 100% | ≈2000 grams |

To the 148.6 grams of AQUACOAT brand of ethyl cellulose as a 30% solids dispersion in water contained in a mixing vessel equipped with a paddle mixer and a Lightnin mixer were added the 4.4 grams of dibutyl sebacate and the dispersion was mixed for 10 minutes. The 125 grams of acetaminophen prescreened through 20 mesh (Tyler) followed by 200 grams of deionized water were added and mixed for one hour. The remaining water, 1522 grams, was then added and the dispersion was transferred to the feed hopper of the Niro Portable Spray Drier used in Example 2.

The spray drier was operated such that an air inlet temperature of approximately 200°–210° C. was maintained throughout the run. An air outlet temperature was recorded at 85°–95° C.

The product was a fine, white powder which had a neutral taste.

EXAMPLE 4

This example describes the preparation of fast dissolving dosage forms using the spray dried taste-neutral acetaminophen of Example 1 and other ingredients as follows:

| Ingredients | Weight % suspension | Grams Ingredient per 500 grams suspension |
|---|---|---|
| Gelatin, BY 19/50 | 4.0 | 20.00 |
| Mannitol, granular | 3.0 | 15.00 |
| Deionized water | 67.5 | 337.5 |
| NUTRASWEET, NF | 0.6 | 3.00 |
| Anise/Juicy Fruit #669 | 0.75 | 3.75 |
| Red FD&C #40 (1% Solution) | 0.25 | 1.25 |
| Sodium lauryl sulfate | 1.0 | 5.00 |
| Sweetness Flavor #284 | 0.1 | 0.5 |
| Powder, Example 2 | 22.8 | 114 |
| Total: | 100 | 500 |

The procedure for preparing a batch of the above suspension takes place in two stages, i.e. the preparation of the gelatin base and the addition of the pharmaceutical agent.

The gelatin base is prepared by adding the gelatin to the deionized water at 30° C. and mixing until the gelatin is dissolved. The solution is then cooled to 25° C. and the mannitol, the sodium lauryl sulfate, the sweetener, and the flavors are separately added and dissolved.

The freeze drier employed in this example was a Virtis 25 SRC Model Freeze Drier. The fast dissolving dosage forms were prepared by dosing 500 milligrams of the suspension of acetaminophen into each well in a thermoformed blister tray containing 10 wells per tray. The filled trays were placed in a larger tray containing a dry ice-methanol mixture. When the suspension in the wells were frozen, the samples were placed on the freeze dryer trays at a shelf temperature of −45° C.

When the samples had reached a temperature of −45° C., as determined by a probe in a well, the condenser was turned on and the freezer turned off. The condenser temperature was brought to between −40° and −45° C. and the vacuum was turned on to between 50 and 60 millitorrs. The heater was then turned on and the shelf temperature was adjusted to 50°–55° C. The heat-dry cycle lasted for 4 hours. The vacuum, the condenser and the heater were turned off and the samples removed. The wafers from each batch were removed from the wells in the trays. They were white in color and each weighed about 165 milligrams of which about 80 milligrams was acetaminophen. The wafers from each batch when placed on the tongue exhibited a fruit flavor with a very slight bitter after taste. When placed in water at 37° C. the wafers disintegrated in less than ten seconds.

EXAMPLE 5

This example describes the preparation of a chewable tablet using the spray dried taste neutral acetaminophen of Example 1 and other ingredients as follows:

| Ingredients | Weight |
| --- | --- |
| Powder of Example 2, 70% | 500 mg |
| Aluminum Stearate | 2 mg |
| Sorbitol | q.s. to 700 mg |
| Total | 700 mg |

The powder of Example 1 contained 70% by weight or 350 mg of acetaminophen. The ingredients are mixed in a suitable mixer and formed into tablets. The tablets when chewed in the mouth have a neutral taste and good mouthfeel. The taste could be improved by incorporation into the tablet of suitable flavoring agents such as a mint flavoring agent.

We claim:

1. In a pharmaceutical dosage form for oral administration as a solid, which dosage form can be disintegrated by water within ten seconds, the improvement which comprises incorporating into such dosage form as the pharmaceutical substance a therapeutic taste-neutral powder form of spray-dried acetaminophen which consists essentially of, based upon the weight of the powder, about 63% to 77% by weight acetaminophen, about 15% to 30% by weight of ethyl cellulose and about 2% to 7% by weight of a plasticiser the powder having been spray dried from a dispersion of the acetaminophen and ethyl cellulose in water having a plasticiser dissolved or suspended therein.

2. In a pharmaceutical dosage form for oral administration as a solid chewable taste-neutral tablet containing acetaminophen, the improvement which comprises incorporating into such tablet as the pharmaceutical substance a therapeutic taste-neutral powder form of spray-dried acetaminophen which consists essentially of, based upon the weight of the powder, about 63% to 77% by weight acetaminophen, about 15% to 30% by weight ethyl cellulose and about 2% to 7% by weight of a plasticiser, the powder having been spray dried from a dispersion of the acetaminophen and ethyl cellulose in water having a plasticiser dissolved or suspended therein.

3. The dosage form of claim 1 wherein the plasticiser is dibutyl sebacate.

4. The dosage form of claim 2 wherein the plasticiser is dibutyl sebacate.

* * * * *